(12) United States Patent
Taguchi et al.

(10) Patent No.: US 8,257,570 B2
(45) Date of Patent: Sep. 4, 2012

(54) ELECTROPHORESIS CHIP AND ELECTROPHORESIS UNIT HAVING THE SAME

(75) Inventors: Takayuki Taguchi, Kyoto (JP); Shigeru Kitamura, Kyoto (JP); Hiroshi Fukuya, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 12/686,192

(22) Filed: Jan. 12, 2010

(65) Prior Publication Data

US 2010/0108520 A1 May 6, 2010

Related U.S. Application Data

(62) Division of application No. 11/587,151, filed as application No. PCT/JP2005/008015 on Apr. 27, 2005, now Pat. No. 7,790,008.

(30) Foreign Application Priority Data

Apr. 28, 2004 (JP) ................. 2004-133281

(51) Int. Cl.
*G01N 27/26* (2006.01)
(52) U.S. Cl. .................. 204/604; 204/601; 422/502
(58) Field of Classification Search .......... 204/600, 204/601, 604; 422/502–508
See application file for complete search history.

(56) References Cited

U.S. PATENT DOCUMENTS

| | | | | |
|---|---|---|---|---|
| 5,858,195 | A * | 1/1999 | Ramsey | 204/601 |
| 5,993,750 | A | 11/1999 | Ghosh et al. | |
| 6,167,910 | B1 | 1/2001 | Chow et al. | 137/827 |
| 6,321,791 | B1 | 11/2001 | Chow | |
| 2002/0074271 | A1 | 6/2002 | Hu et al. | |
| 2002/0112961 | A1 | 8/2002 | O'Connor et al. | |
| 2002/0137218 | A1* | 9/2002 | Mian et al. | 436/45 |
| 2003/0175162 | A1 | 9/2003 | Anazawa et al. | |
| 2004/0109793 | A1 | 6/2004 | McNeely et al. | |
| 2006/0153745 | A1* | 7/2006 | Ermakov | 422/130 |

FOREIGN PATENT DOCUMENTS

| | | |
|---|---|---|
| JP | H08-178897 | 12/1996 |
| JP | H08-327594 A | 12/1996 |
| JP | 11-5029 A | 1/1999 |
| JP | 11-148919 A | 6/1999 |
| JP | 2002-86399 | 3/2002 |
| JP | 2002-131279 | 5/2002 |

(Continued)

OTHER PUBLICATIONS

C. Chaiyasut, et al., "Red Blood Cell Lysis at the Single Cell Level by Using a Mini Electrophoresis Apparatus", Chromatography, vol. 23, No. 1, 2002, pp. 33-38.

(Continued)

*Primary Examiner* — J. Christopher Ball
(74) *Attorney, Agent, or Firm* — Morgan, Lewis & Bockius LLP

(57) ABSTRACT

In order to provide a high-performance electrophoresis chip and an electrophoresis unit having the same that can restrain the diffusion of sample at an intersection between the electrophoresis groove and the sample introduction groove and prevent decrease in contrast and decrease in resolution, an electrophoresis chip is provided with a sample introduction groove, an electrophoresis groove, and a through hole. The sample introduction groove, the electrophoresis groove, and the through hole are formed on different substrates. In the electrophoresis chip, by combining the substrates, the sample introduction groove and the electrophoresis groove are located in different planes.

4 Claims, 13 Drawing Sheets

FOREIGN PATENT DOCUMENTS

| | | | |
|---|---|---|---|
| JP | 2002-304605 A | 10/2002 |
| JP | 2003-28836 | 1/2003 |
| JP | 2003-114229 A | 4/2003 |
| JP | 2003-527972 | 9/2003 |
| JP | 2003-324665 | 11/2003 |
| WO | WO 01/25137 A1 | 4/2001 |
| WO | WO 01/25138 A1 | 4/2001 |
| WO | WO 03/015890 | 2/2003 |

OTHER PUBLICATIONS

Final Office Action for related U.S. Appl. No. 12/686,155 dated Jun. 7, 2011.

Supplementary European Search Report dated Sep. 6, 2011 in the corresponding European Patent Application No. 05736721.1.

Office Action issued in a related U.S. Appl. No. 12/686,155, dated Jan. 26, 2012.

* cited by examiner

ELECTROPHORESIS CHIP AND ELECTROPHORESIS UNIT HAVING THE SAME

CROSS-REFERENCE TO RELATED APPLICATIONS

This application is a divisional application of U.S. patent application Ser. No. 11/587,151 filed Oct. 20, 2006, which is a national phase filing of PCT/JP05/08015 filed Apr. 27, 2005. U.S. patent application Ser. No. 11/587,151 claims priority under 35 U.S.C. §119(a) to Japanese Patent Application No. 2004-133281 filed Apr. 28, 2004. The entire disclosures of U.S. patent application Ser. No. 11/587,151, PCT/JP05/08015, and Japanese Patent Application No. 2004-133281 are hereby incorporated herein by reference.

BACKGROUND OF THE INVENTION

1. Field of the Invention

The present invention relates to an electrophoresis chip and an electrophoresis unit having the same for analyzing blood components, protein, and nucleic acids.

2. Background Information

Conventionally, electrophoresis units provided with electrophoresis chips have been used to precisely analyze protein, nucleic acids and so on.

The electrophoresis chips of electrophoresis units generally have an electrophoresis groove and a sample introduction groove on one substrate (refer to Unexamined Patent Publication H08-178897 (published on Jul. 12, 1996).

When samples are analyzed with electrophoresis chips of this type, an electrophoresis liquid is introduced into electrophoresis grooves, and a sample is introduced into the sample introduction groove, for example. Then, a voltage is applied between ends of the sample introduction groove to move the sample to an intersection with the electrophoresis groove by electrophoresis, and then another voltage is applied between ends of the electrophoresis groove to move the sample through the electrophoresis groove.

Because each component contained in the sample that is moving through the electrophoresis groove has different electrophoretic speeds according to its size, ion composition, and so on, each of the components is separated from one another in the electrophoresis groove. This makes it possible to detect and analyze separated desired components only by introducing small quantities of the sample.

The conventional electrophoresis chip has, however, problems described hereinafter.

Specifically, in the electrophoresis chip disclosed in the above-mentioned patent publication, the electrophoresis groove and the sample introduction groove simply intersect each other at an intersection, i.e., there are no means to block the travel of the liquid that reciprocates between each groove. Accordingly, when the sample is electrophoresed in the electrophoresis groove after it is moved through the sample introduction groove to the intersection, the sample might to be diffused from the intersection in every direction. The diffusion of the sample will be a cause of decreasing contrast and resolution at the sample analysis.

SUMMARY OF THE INVENTION

It is an object of the present invention to provide an electrophoresis chip and an electrophoresis unit having the same, where it is possible to prevent the decrease contrast and resolution by reducing the diffusion of the sample at the intersection between the sample introduction groove and the electrophoresis groove.

An electrophoresis chip according to a first aspect of the invention electrophoreses a sample to be analyzed. The electrophoresis chip comprises a first sample introduction groove, a second sample introduction groove, a first electrophoresis groove, a second electrophoresis groove, and a through hole. The sample is introduced into the first sample introduction groove. The sample is thereafter introduced into the second sample introduction groove. The second sample introduction groove is formed in a plane different from a plane in which the first sample introduction groove is formed. The first electrophoresis groove is located along a direction that intersects with at least one of the first sample introduction groove and the second sample introduction groove. The second electrophoresis groove is located along a direction that intersects with at least one of the first sample introduction groove and the second sample introduction groove. The second electrophoresis groove is formed in a plane different from a plane in which the first electrophoresis groove is formed. The through hole connects the first sample introduction groove with the second sample introduction groove. The through hole connects the first electrophoresis groove and the second electrophoresis groove with each other.

In this aspect, each of the electrophoresis groove and the sample introduction groove is divided into halves. One of the sample introduction grooves and the other are formed in different planes, and one of the electrophoresis grooves and the other are formed in different planes. The first sample introduction groove and the second sample introduction groove that are formed in the different planes, and the first electrophoresis groove and the second electrophoresis groove that are formed in the different planes are connected via one through hole. In other words, the first sample introduction groove, the second sample introduction groove, the first electrophoresis groove, and the second electrophoresis groove are communicated with each other via one through hole.

For example, when a voltage is applied to two ends of the first sample introduction groove and the second sample introduction groove that are not connected with each other (both ends if the first and second sample introduction grooves are considered to be one groove) and a sample to be analyzed is introduced into one end, the sample is introduced to the other end via the through hole. Next, when a voltage is applied to two ends of the first electrophoresis groove and the second electrophoresis groove that are not connected with each other (both ends if the first and the second electrophoresis grooves are considered to be one groove), the sample introduced in the through hole, which connects the first sample introduction groove with the second sample introduction groove and connects the first electrophoresis groove with the second electrophoresis groove, is separated by electrophoresis.

As described above, since the separation and analysis are performed by electrophoresis by introducing the sample into the common through hole that connects the first and second sample introduction grooves with each other and the first and second electrophoresis grooves with each other, it is possible to reduce the amount of diffusion of the sample introduced into the through hole into the electrophoresis liquid, compared to the conventional electrophoresis chip in which the sample introduction groove and the electrophoresis groove are simply intersect with each other in a single plane. The reason is that a rate of the sample in contact with the electrophoresis liquid to the whole sample is reduced by extending the through hole. As a result, it is possible to prevent problems from occurring such as decrease in contrast or decrease in resolution when the sample separated by electrophoresis is analyzed.

Furthermore, since the separation process can be performed by electrophoresis using the sample introduced into the through hole, it is possible to perform the separation and analysis while ensuring a more stable amount of the sample at every test, compared to the conventional electrophoresis chip in which the sample introduction groove and the electrophoresis groove simply intersect with each other in one plane.

An electrophoresis chip according to a second aspect of the present invention is the electrophoresis chip according to the first aspect, wherein the through hole is configured to have a cross section where a length in a direction in which the sample is separated by electrophoresis is shorter than a length in a direction in which the sample is introduced.

In this aspect, a cross-sectional shape of the common through hole connecting the first and second sample introduction grooves and the first and second electrophoresis grooves is defined.

Specifically, the cross section of the through hole is configured such that the through hole has a direction in which the sample is introduced and a separating direction by electrophoresis, and a length in the separating direction by electrophoresis in a cross-sectional shape is shorter than a length of the direction in which the sample is introduced in a cross-sectional shape.

As a result, it is possible to reduce the diffusion of the sample that is introduced into the through hole into directions other than the separation direction during electrophoresis, thereby making it possible to more precisely analyze components.

An electrophoresis chip according to a third aspect of the invention is the electrophoresis chip according to the first or second aspect, wherein the first sample introduction groove and the first electrophoresis groove are formed on one substrate.

In this aspect, a positional relationship between the first sample introduction groove and the first electrophoresis groove is defined.

Since the first sample introduction groove and the first electrophoresis groove are formed on one substrate as described above, it is possible to minimize the number of substrates, thereby simplifying the structure and cutting down on costs.

An electrophoresis chip according to a fourth aspect of the invention is the electrophoresis chip according to any of the first through third aspects, wherein the second sample introduction groove and the second electrophoresis groove are formed on one substrate.

In this aspect, a positional relationship between the second sample introduction groove and the second electrophoresis groove is defined.

Since the second sample introduction groove and the second electrophoresis groove are formed on one substrate as described above, it is possible to minimize the number of substrates, thereby simplifying the structure and cutting down on costs. Especially, since the second sample introduction groove and the second electrophoresis groove are formed on another substrate as well as forming the first sample introduction groove and first electrophoresis groove on one substrate, it is possible to configure an electrophoresis chip according to the present invention by three substrates that are formed by combining them with the substrate in which the through hole is formed.

An electrophoresis chip according to a fifth aspect of the invention is the electrophoresis chip according to the third or fourth aspect, wherein a pretreatment unit is formed on the substrate for pretreating the sample.

In this aspect, the pretreatment unit that pretreats the sample is formed on the substrate on which the sample introduction groove is formed.

Accordingly, since the pretreatment unit can be formed without concern for a portion where the electrophoresis groove is formed, it is possible to downsize the electrophoresis chip and obtain integrated electrophoresis chips compared to a case in which pretreatment unit is formed on an electrophoresis chip that has the electrophoresis groove and the sample introduction groove on one substrate.

An electrophoresis chip according to a sixth aspect of the invention applies a voltage between ends of a groove into which an electrophoresis liquid is introduced to electrophorese a sample to be analyzed. The electrophoresis chip comprises a sample introduction groove and an electrophoresis groove. Into the sample introduction groove, the sample to be analyzed is introduced. The electrophoresis groove is located along a direction that intersects with the sample introduction groove, and has both ends to which a voltage is applied to separate the sample by electrophoresis. The sample introduction groove and the electrophoresis groove are formed in different planes.

In this aspect, the sample introduction groove and the electrophoresis groove are located in different planes three-dimensionally.

The conventional electrophoresis chip is typically configured such that the sample introduction groove and the electrophoresis groove are formed in one plane and simply intersect with each other. Accordingly, it is likely that the sample introduced into the sample introduction groove and the electrophoresis liquid within the electrophoresis groove are mixed and the sample is diffused. Furthermore, in the case that the sample to be analyzed is pretreated in advance of performing the analysis with the electrophoresis chip, if the pretreatment unit is formed on the same substrate to obtain an integrated chip, the chip cannot avoid its upsizing.

Therefore, in the electrophoresis chip according to the present invention, the sample introduction groove and the electrophoresis groove are placed in different planes, not in the same plane.

Accordingly, it is possible to reduce the diffusion of sample at the intersection between the sample introduction groove and the electrophoresis groove, compared to a structure in which the sample introduction groove and the electrophoresis groove simply intersect with each other in one plane. Furthermore, since the sample introduction groove and the electrophoresis groove can be formed on different substrates, even if the pretreatment unit is formed on one substrate for integration, it is possible to form the pretreatment unit at any positions on the substrate on which the sample introduction groove is formed except for a position where the sample introduction groove is formed. As a result, since it is possible to form the pretreatment unit without concern for the portion where the electrophoresis groove is formed, it is possible to achieve a size reduction of the electrophoresis chip, compared to the electrophoresis chip having a structure in which both grooves are formed in one plane.

An electrophoresis chip according to a seventh aspect of the invention is the electrophoresis chip according to the sixth aspect further comprises a through hole located at an intersection between the electrophoresis groove and the sample introduction groove in plan view, for communicating the electrophoresis groove with the sample introduction groove.

In this aspect, the sample introduction groove and the electrophoresis groove located in different planes three-dimensionally are communicated via the through hole communicating both grooves with each other.

More specifically, when the analysis is performed with the electrophoresis chip according to the present invention, the sample introduced into one end of the sample introduction groove is moved to a connection portion with the through hole communicating with the electrophoresis groove by applying a voltage between ends of the sample introduction groove. Then, while the sample is distributed at the connection portion between the through hole and the electrophoresis groove, a voltage is applied between ends of the electrophoresis groove. Accordingly, components contained in the sample are moved through the electrophoresis groove at different speeds depending on different sizes or ion compositions, so that the components can be separated in the electrophoresis groove. By detecting and analyzing the separated components, it is possible to perform a precise analysis easily by just introducing small amounts of sample.

In the electrophoresis chip according to the present invention, the sample introduction groove and the electrophoresis groove are communicated with each other via the through hole. Accordingly, it is possible to reduce the diffusion of sample at the intersection between the sample introduction groove and the electrophoresis groove more effectively.

It is preferable that the through hole has a minimum length to prevent the diffusion of sample because it is necessary for the sample that has been moved through the sample introduction groove to move toward the electrophoresis groove at the through hole at a pre-stage when a voltage is applied between ends of the electrophoresis groove. Alternatively, it is preferable that the sample introduction groove is located above the electrophoresis groove. In this structure, it is possible to move the sample that has been moved to the connection portion of the sample introduction groove with the through hole toward the electrophoresis groove by gravity or capillary force.

An electrophoresis chip according to an eighth aspect of the invention is the electrophoresis chip according to the sixth or seventh aspect further comprising a valve mechanism in the through hole for preventing a mixture of an electrophoresis liquid introduced into the electrophoresis groove and a sample introduced into the sample introduction groove.

In this aspect, the valve mechanism, which is located at the intersection between the sample introduction groove and the electrophoresis groove, e.g., the through hole communicating the sample introduction groove with the electrophoresis groove, can prevent the diffusion of sample due to the mixture of the sample and the electrophoresis liquid.

In a case that the sample introduction groove and the electrophoresis groove that are placed in different planes three-dimensionally simply intersect with each other, the sample that is moved through the sample introduction groove to the intersection by electrical injection may be diffused from the sample introduction groove in every direction of the electrophoresis grooves and the sample introduction grooves at a pre-stage when a voltage is applied between ends of the electrophoresis groove.

Therefore, in the electrophoresis chip according to the present invention, the valve mechanism is provided in the through hole, e.g., at the intersection between both grooves, and the valve mechanism is changed into an open state immediately before applying a voltage between ends of the electrophoresis groove. As a result, it is possible to prevent the diffusion of sample, thereby preventing the generation of poor contrast in the electrophoretic pattern or the decrease in resolution.

An electrophoresis chip according to a ninth aspect of the invention applies a voltage between ends of a groove into which an electrophoresis liquid is introduced to electrophorese a sample to be analyzed. The electrophoresis chip comprises a sample introduction groove, an electrophoresis groove, and a valve mechanism. The sample to be analyzed is introduced into the sample introduction groove. The electrophoresis groove is located along a direction that intersects with the sample introduction groove, and has both ends to which a voltage is applied to separate the sample by electrophoresis. The valve mechanism is located at an intersection between the electrophoresis groove and the sample introduction groove, and prevents a mixture of the electrophoresis liquid and the sample.

In this aspect, the valve mechanism is provided that prevents a mixture of the electrophoresis liquid and the sample at the intersection between the sample introduction groove and the electrophoresis groove.

The conventional electrophoresis chip is configured such that the sample introduction groove and the electrophoresis groove that are formed in a single plane simply intersect with each other. Accordingly, the sample introduced into the sample introduction groove might be diffused in every direction at the intersection between the sample introduction groove and the electrophoresis groove. It is quite likely that the sample is diffused when an aqueous solution is used as an electrophoresis liquid, and the diffusion may cause problems such as decrease in contrast of the electrophoretic pattern or decrease in resolution.

Therefore, in the electrophoresis chip according to the present invention, the valve mechanism is provided so as to partition the sample introduction groove from the electrophoresis groove, so that the sample is prevented from being diffused in advance of the start of electrophoresis. Consequently, it is possible to prevent the diffusion of sample by changing the valve mechanism to an open state immediately before applying a voltage between ends of the electrophoresis groove. As a result, it is possible to prevent the generation of poor contrast in the electrophoretic pattern or the decrease in resolution due to the diffusion of sample.

An electrophoresis chip according to a tenth aspect of the invention is the electrophoresis chip according to the eighth or ninth aspect, wherein the valve mechanism can be changed into an open state by using any of mechanical, electrical, and optical means.

In this aspect, it is possible to change the valve mechanism to an open state mechanically, electrically, or optically at timing when a voltage is applied between ends of the electrophoresis groove. As a result, it is possible to prevent the generation of poor contrast in the electrophoretic pattern and the decrease in resolution due to the mixture of the sample and the electrophoresis liquid.

An electrophoresis chip according to an eleventh aspect of the invention is the electrophoresis chip according to the tenth aspect, wherein the valve mechanism can be opened and closed repeatedly.

In this aspect, since the valve mechanism can be opened and closed by the mechanical, electrical, or optical means repeatedly, it is possible to use the electrophoresis chip repeatedly. As a result, even if the electrophoresis chip is applied to an expensive one, it can cut down on costs by using it repeatedly.

An electrophoresis chip according to a twelfth aspect of the invention is the electrophoresis chip according to the tenth aspect, wherein the valve mechanism includes a membrane that can be opened by light.

In this aspect, by applying laser to the light opening membrane to destroy it at timing when a voltage is applied between ends of the electrophoresis groove, it is possible to change the valve mechanism to an open state easily. As a result, it is possible to prevent the generation of poor contrast in the electrophoretic pattern or the decrease in resolution due to the diffusion of sample.

If the light opening membrane is employed as a valve mechanism, it is preferable that the membrane is mainly applied to disposable electrophoresis chips because it is difficult to change the membrane back to a closed state after it is changed to an open state by applying the laser.

An electrophoresis chip according to a thirteenth aspect of the invention is the electrophoresis chip according to any of the first through twelfth aspects, wherein the electrophoresis liquid is an aqueous solution.

Typically, if an aqueous solution is employed as an electrophoresis liquid, the sample and the electrophoresis liquid are likely to be mixed with each other at the intersection between the sample introduction groove and the electrophoresis groove, and the sample is highly likely to be diffused.

However, since the electrophoresis chip according to the present invention is configured such that the sample is unlikely to be diffused into the electrophoresis liquid at the intersection between the sample introduction groove and the electrophoresis groove, it is possible to prevent a mixture of the electrophoresis liquid and the sample. As a result, even if the aqueous solution is employed as an electrophoresis liquid, it is possible to obtain an electrophoresis chip having high contrast and high resolution.

An electrophoresis chip according to a fourteenth aspect of the invention is the electrophoresis chip according to any of the sixth to thirteenth aspects further comprises a first substrate on which the electrophoresis groove is formed, and a second substrate on which the sample introduction groove is formed.

In this aspect, the electrophoresis groove and the sample introduction groove are formed on different substrates. Accordingly, it is possible to easily realize an electrophoresis chip having a three-dimensional structure in which the sample introduction groove and the electrophoresis groove are formed in different planes by combining these substrates.

An electrophoresis chip according to a fifteenth aspect of the invention is the electrophoresis chip according to the fourteenth aspect, wherein the first substrate and the second substrate are oriented parallel to each other.

In this aspect, since the first substrate on which the electrophoresis groove is formed and the second substrate on which the sample introduction groove is formed are placed parallel to each other, it is possible to realize a thin electrophoresis chip having a three-dimensional structure in which the sample introduction groove and the electrophoresis groove are formed in different planes.

An electrophoresis chip according to the sixteenth aspect of the invention is the electrophoresis chip according to the fourteenth or fifteenth aspect, wherein a pretreatment unit is formed on the second substrate for pretreating the sample.

In this aspect, the pretreatment unit that pretreats the sample is formed on the second substrate on which the sample introduction groove is formed. Consequently, since the pretreatment unit can be formed without concern for a portion where the electrophoresis groove is formed, it is possible to downsize electrophoresis chips to obtain integrated electrophoresis chips, compared to a case in which a pretreatment unit is formed on one substrate of the electrophoresis chip on which the electrophoresis groove and the sample introduction groove are formed.

An electrophoresis chip according to a seventeenth aspect of the invention is the electrophoresis chip according to the fifth or the sixteenth aspect, wherein the pretreatment unit performs a process of destroying erythrocytes of blood to take out hemoglobin.

In this aspect, as a pretreatment, the process is performed of destroying erythrocytes contained in blood as a stage in advance of measuring hemoglobin A1c. Accordingly, it is possible to take out hemoglobin A1c to measure the amount of hemoglobin A1c just by introducing the blood into one chip to separate components by electrophoresis.

An electrophoresis unit according to an eighteenth aspect of the invention comprises the electrophoresis chip set forth in any of the first through seventeenth aspects, a detection unit, and an analysis unit. The detection unit detects components contained in the sample that is separated in the electrophoresis groove. The analysis unit analyzes the components detected by the detection unit.

In this aspect, since the electrophoresis chip that makes it possible to realize more downsizing and integration is provided, the electrophoresis unit can be downsized, too. If the electrophoresis chip with the valve mechanism is provided, even if the aqueous solution is employed as an electrophoresis liquid, for example, it is possible to prevent a mixture of the sample and the electrophoresis liquid, thereby obtaining electrophoresis units having no poor contrast and having a high resolution.

Figure 1:
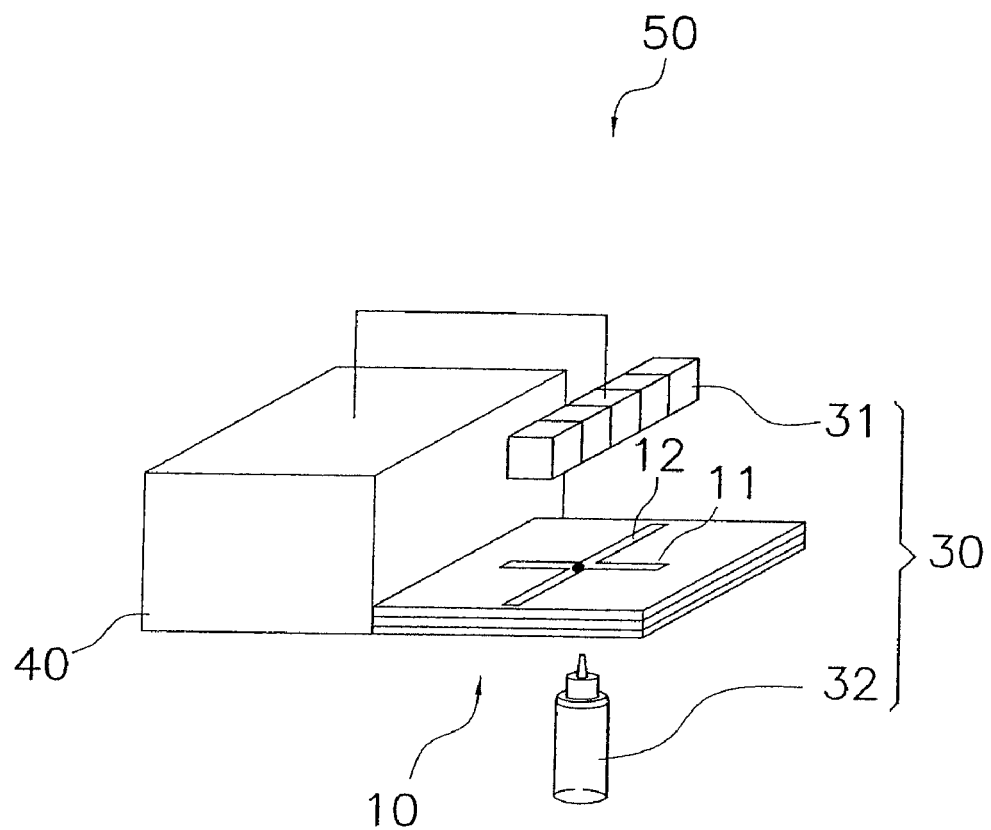
FIG. 1 is a perspective view of a schematic structure of the electrophoresis unit having the electrophoresis chip according to one embodiment of the present invention.

LIST OF REFERENCE NUMERALS electrophoresis chip 10
substrate (second substrate) 10*a*
substrate 10*b*
substrate (first substrate) 10*c*
sample introduction groove 11 openings 11a and 11b
electrophoresis groove 12
openings 12a and 12b
through hole 13
valve mechanism 14
light opening membrane 14a
irradiation unit 14b
pretreatment unit 20
mix diffusion dilution unit 21
pretreatment liquid reservoir 22a
electrophoresis liquid reservoir 22b
introduction hole 23
sample-before-pretreatment introduction groove 24
pretreatment liquid introduction groove 25
air holes 26a, 26b, 26c and 26d
detection unit 27
detection unit 30
light receiving unit 31
laser irradiating unit 32
analysis unit 40
electrophoresis unit 50
electrophoresis chip 60
substrate (second substrate) 60a
substrate 60b
substrate (first substrate) 60c
sample introduction groove 61
electrophoresis groove 62
openings 62a and 62b
through hole 63
electrophoresis chip 70
substrate 70a
substrate 70b
substrate 70c
first sample introduction groove 71a
second sample introduction groove 71b
first electrophoresis groove 72a
second electrophoresis groove 72b
through hole 73
openings 74a and 74b
openings 75a and 75b

DETAILED DESCRIPTION OF THE INVENTION

First Embodiment

A description is now provided for an electrophoresis chip 10 and an electrophoresis unit 50 having the same according to one embodiment of the present invention with reference to FIGS. 1 through 4.

Structure of the Electrophoresis Unit

The electrophoresis unit 50 according to the present embodiment is an analysis device that is provided with the electrophoresis chip 10 according to the present invention to precisely analyze blood, protein, nucleic acids and so on in samples.

The electrophoresis unit 50 is provided with the electrophoresis chip 10, a detection unit 30, and an analysis unit 40, as shown in FIG. 1.

Figure 2:
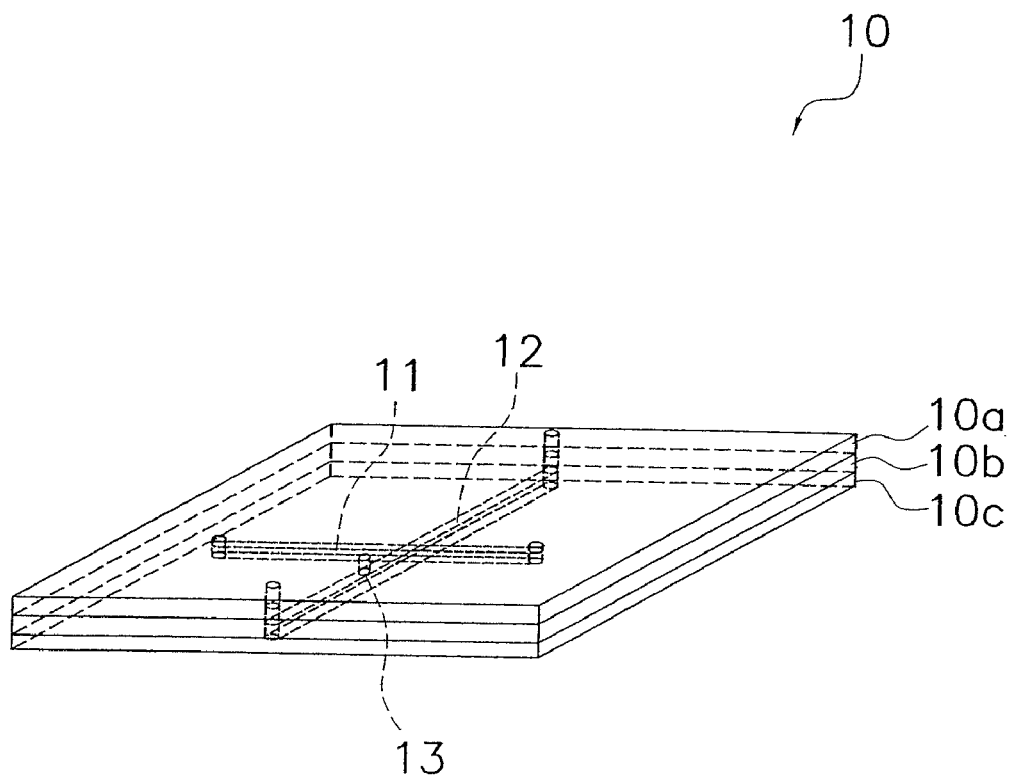
FIG. 2 is a perspective view of a structure of the electrophoresis chip shown in FIG. 1.

The electrophoresis chip 10 is provided with a sample introduction groove 11, an electrophoresis groove 12, and a through hole 13 as shown in FIG. 2. The electrophoresis chip 10 separates each component contained in the sample by applying a voltage between ends of the sample introduction groove 11 to move the sample through the sample introduction groove 11 by electrophoresis.

It should be noted that the structure of the electrophoresis chip 10 will be described in greater detail below.

The detection unit 30 is provided with a light receiving unit 31 and a laser irradiating unit 32. The light receiving unit 31 is located on an opposite side of the laser irradiating unit 32 across the electrophoresis chip 10, and detects a transmitted light from laser light applied to the sample in the electrophoresis groove 12. The laser irradiating unit 32 applies the laser light to each separated component in the electrophoresis groove 12.

The analysis unit 40 includes an A/D converter, a CPU and among other things (not illustrated) therein. The A/D converter coverts optical signals of the transmitted light, which are detected at the light receiving unit 31 and amplified after the detection, into digital signals. The CPU receives the digital signals, which are converted from the optical signals by the A/D converter, and distributions or a likeness corresponding to the electrophoresis groove 12 are displayed on a monitor as an analysis output of the components being analyzed.

Structure of the Electrophoresis Chip

The electrophoresis chip 10 according to the present embodiment is provided with the sample introduction groove 11, the electrophoresis groove 12 and the through hole 13, as mentioned above, which are located each in different planes three-dimensionally (see FIG. 2).

Figure 3:
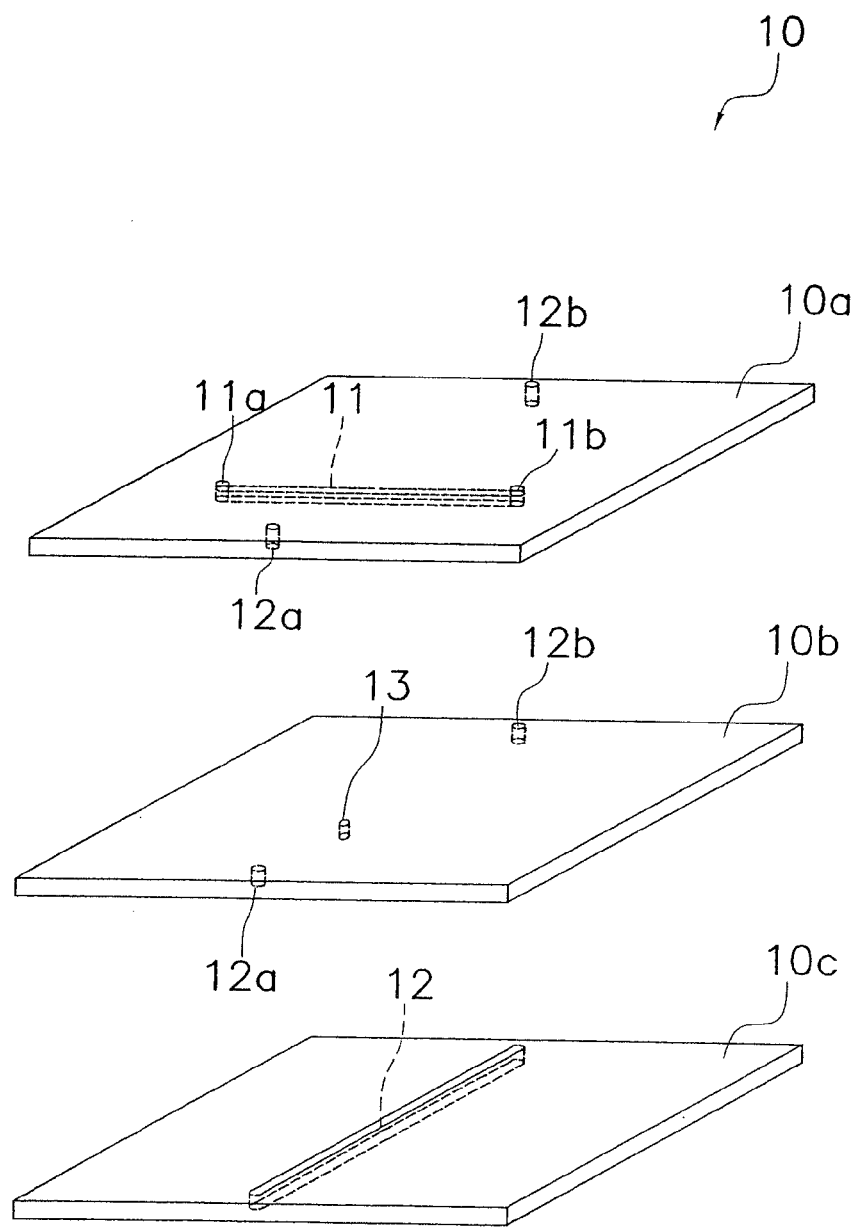
FIG. 3 is an exploded perspective view in which the substrates of the electrophoresis chip in FIG. 2 are shown separated from one another.

As shown in FIG. 3, the sample introduction groove 11, the electrophoresis groove 12, and the through hole 13 are formed on different substrates 10a to 10c, and the substrates 10a to 10c are combined to locate the sample introduction groove 11 and the electrophoresis groove 12 in different planes three-dimensionally.

The substrate (second substrate) 10a is formed with the sample introduction groove 11, openings 11a and 11b, and openings 12a and 12b. It should be noted that the openings 11a, 11b, 12a, and 12b are formed by etching the substrate 10a, for example, as in the case with the sample introduction groove 11.

The substrate 10b is formed with the through hole 13 and the openings 12a and 12b.

The substrate (a first substrate) 10c is formed with the electrophoresis groove 12 by etching, for example, as in the case with the sample introduction groove 11 on the substrate 10a.

The sample introduction groove 11 is formed on a contact surface of the substrate 10a with the substrate 10b by etching, for example. By combining the substrate 10a and the substrate 10b together, a capillary is defined between a portion corresponding to the sample introductions groove 11 and the substrate 10b. The sample introduction groove 11 is connected with the openings 11a and 11b formed on the substrate 10a. A sample to be analyzed is introduced by pressure or electrical injection into the openings 11a and 11b. If the electrical injection is employed, electrodes (not illustrated) are connected to both ends of the sample introduction groove 11 to apply a voltage thereto.

The electrophoresis groove 12 is formed on a contact surface of the substrate 10c with the substrate 10b by etching, for example, as in the case of the sample introduction groove 11. The groove 12 is connected to the openings 12a and 12b. By combining the substrate 10c and the substrate 10b together, a capillary is defined between a portion corresponding to the electrophoresis groove 12 and the substrate 10b. The openings 12a and 12b are formed on the substrate 10a and 10b, respectively, and electrodes (not illustrated) are connected to both ends of them to apply a voltage thereto.

The through hole 13 is a hole penetrating through the substrate 10b in a perpendicular direction to communicate the sample introduction groove 11 with the electrophoresis groove 12. Moreover, the through hole 13 is provided with a valve mechanism 14 to prevent a mixture of the sample in the sample introduction groove 11 and the electrophoresis liquid in the electrophoresis groove 12, and the diffusion of the sample (refer to FIG. 4).

Figure 4:
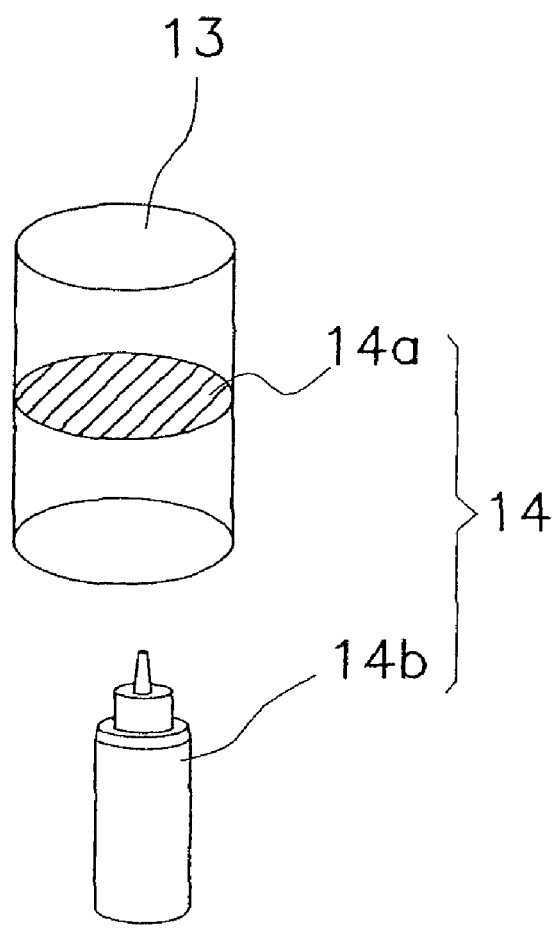
FIG. 4 is a perspective view of a valve mechanism of the electrophoresis chip in FIG. 2.

As shown in FIG. 4, the valve mechanism 14 includes a light opening membrane 14a positioned to partition the sample introduction groove 11 from the electrophoresis groove 12, and an irradiation unit 14b to apply laser light to the light opening membrane 14a. In the valve mechanism 14, the light opening membrane 14a contains dye, and the irradiation unit 14b irradiates the light opening membrane 14a with the laser light in order to change to an open state. Then, the dye contained in the light opening membrane 14a absorbs heat of the laser light and the light opening membrane 14a is destroyed, thereby the valve mechanism 14 can be changed to an open state in which the sample introduction groove 11 and the electrophoresis groove 12 communicate with each other. In place of the irradiation unit 14b, the laser irradiating unit 32 of the detection unit 30 may be used.

Analysis by the Electrophoresis Unit

In the electrophoresis unit 50 according to the present embodiment, blood components, protein or the like are analyzed by the following procedure.

First, the electrophoresis chip 10, in which the sample introduction groove 11 and the electrophoresis groove 12 are filled with the electrophoresis liquid, is set onto a rest base of the electrophoresis unit 50, and a sample to be analyzed is introduced into the opening 11a or 11b of the sample introduction groove 11 by pressure or electrical injection.

Next, the electrodes are connected to the openings 11a and 11b at opposite ends of the sample introduction groove 11, and then a voltage is applied to the ends to move the sample to the intersection between the sample introduction groove 11 and the electrophoresis groove 12. At this time, the laser light is applied by the irradiation unit 14b to the light opening membrane 14a of the valve mechanism 14 installed in the through hole 13 so that the light opening membrane 14a is destroyed to communicate the sample introduction groove 11 with the electrophoresis groove 12. Accordingly, the sample can be moved from the through hole 13 toward the electrophoresis groove 12. After that, the electrodes are connected to the openings 12a and 12b at opposite ends of the electrophoresis groove 12, and a voltage is applied to the ends of the electrophoresis groove 12. As a result, the components contained in the sample, which is moved to the intersection between the sample introduction groove 11 and the electrophoresis groove 12, can be separated in the electrophoresis groove 12.

After applying the voltage to the ends of the electrophoresis groove 12 for the predetermined time to separate the components contained in the sample, the laser light is applied to the separated components by the laser irradiating unit 32 of the detection unit 30. The applied laser light transmits through the components and is detected by the light receiving unit 31. Then, the optical signals detected by the light receiving unit 31 are sent to the analysis unit 40.

The analysis unit 40 converts the optical signals sent from the light receiving unit 31 into digital signals, and the built-in CPU displays analysis outputs such as a component distribution based on the digital signals on the monitor.

In the electrophoresis unit 50 according to the present embodiment, with the above-described procedure, the sample introduced into the sample introduction groove 11 can be separated into the components and the components can be analyzed individually.

Features (1) In the electrophoresis chip 10 according to the present embodiment, the sample introduction groove 11 and the electrophoresis groove 12 are placed in the different planes (on the substrates 10a and 10c) three-dimensionally.

According to an analysis using the electrophoresis chip 10 as in the present embodiment, first, the sample, which is introduced into the sample introduction groove 11 by using a method such that a voltage is applied to opposite ends of the sample introduction groove 11, is moved to the intersection with the electrophoresis groove 12. At this stage, at the intersection between the sample introduction groove 11 and the electrophoresis groove 12, the sample and the electrophoresis liquid disposed in the electrophoresis groove 12 might be mixed so that the sample could be diffused from the intersection in every direction, in advance of applying a voltage to the ends of the electrophoresis groove 12. The diffusion of the sample in advance of the start of electrophoresis might cause problems such as decreasing contrast in the electrophoretic pattern of the sample after the analysis or decreasing resolution.

Therefore, in the electrophoresis chip 10 according to the present embodiment, the sample introduction groove 11 and the electrophoresis groove 12 are placed in different planes in order to suppress the diffusion of the sample between the sample introduction groove 11 and the electrophoresis groove 12 before the start of electrophoresis.

Accordingly, it is possible to prevent the sample from being diffused at a pre-stage when starting the electrophoresis by applying the voltage between ends of the electrophoresis groove 12, compared to the conventional structure in which the sample introduction groove 11 and the electrophoresis groove 12 simply intersect with each other in one plane. As a result, it is possible to obtain the high-performance electrophoresis chip 10 by restraining the problems from occurring such as the generation of poor contrast in the electrophoretic pattern and the decrease in resolution due to the diffusion of the sample.

Furthermore, it is possible to form the sample introduction groove 11 and the electrophoresis groove 12 on the separate substrates 10a and 10c respectively by placing the sample introduction groove 11 and the electrophoresis groove 12 in the different planes three-dimensionally. As a result, even if the electrophoresis chip 10 is configured to have an integrated pretreatment unit formed on one substrate (the substrate 10a) on which only the sample introduction groove 11 is formed, for example, it is possible to prevent the chip from being enlarged.

(2) The electrophoresis chip 10 according to the present embodiment is provided with the through hole 13 that communicates the sample introduction groove 11 with the electrophoresis groove 12.

Accordingly, it is possible to restrain the diffusion of sample more effectively because of the communication via the through hole 13 compared to a structure in which the sample introduction groove 11 and the electrophoresis groove 12 directly intersect with each other. As a result, it is possible to prevent problems from occurring such as the poor contrast in the electrophoretic pattern or the decrease in resolution due to the diffusion of sample.

(3) The electrophoresis chip 10 according to the present embodiment is provided with the valve mechanism 14 in the through hole 13 formed at the intersection between the sample introduction groove 11 and the electrophoresis groove 12 to prevent a mixture of the sample in the sample introduction groove 11 and the electrophoresis liquid in the electrophoresis groove 12.

Accordingly, it is possible to prevent the sample from being diffused at the pre-stage when a voltage is applied between ends of the sample introduction groove 11 to start electrophoresis. As a result, it is possible to obtain the high-performance electrophoresis chip 10 by resolving troubles such as poor contrast in the electrophoretic pattern or a decrease in resolution due to the diffusion of the sample.

(4) In the electrophoresis chip 10 according to the present embodiment, as a means to change the valve mechanism 14 to an open state, the light opening membrane 14a and the irradiation unit 14b to apply laser light are used.

Since optical means are used such as the light opening membrane 14a and the irradiation unit 14b to apply laser light, it is possible to change the valve mechanism 14 to an open state by applying the laser light from the irradiation unit 14b to the light opening membrane 14a in timing immediately before applying a voltage between ends of the electrophoresis groove 12. As a result, it is possible to prevent the mixture of the sample and the electrophoresis liquid and the diffusion of sample at a stage before the start of electrophoresis.

Furthermore, since the light opening membrane 14a is used as a valve to partition the sample introduction groove 11 off the electrophoresis groove 12, it is possible to change the valve mechanism 14 to an open state easily just by applying the laser light.

(5) In the electrophoresis chip 10 according to the present embodiment, the sample introduction groove 11 and the electrophoresis groove 12 are formed on the separate substrates 10a and 10c, respectively.

Accordingly, it is possible to realize the electrophoresis chip 10 having a three-dimensional structure.

(6) The electrophoresis unit 50 according to the present embodiment is provided, as described above, with the electrophoresis chip 10, the detection unit 30 to detect the separated components in the electrophoresis chip 10, and the analysis unit 40 to analyze the components detected by the detection unit 30.

Accordingly, it is possible to obtain all effects that are obtained by the electrophoresis chip 10.

Second Embodiment

A description is provided for an electrophoresis chip and an electrophoresis unit having the same according to the present invention with reference to FIGS. 5 through 9. It should be noted that components having the same or similar function to those described in Embodiment 1 will be identified by the same reference numerals for convenience of explanation, and a duplicate explanation will be omitted.

Figure 5:
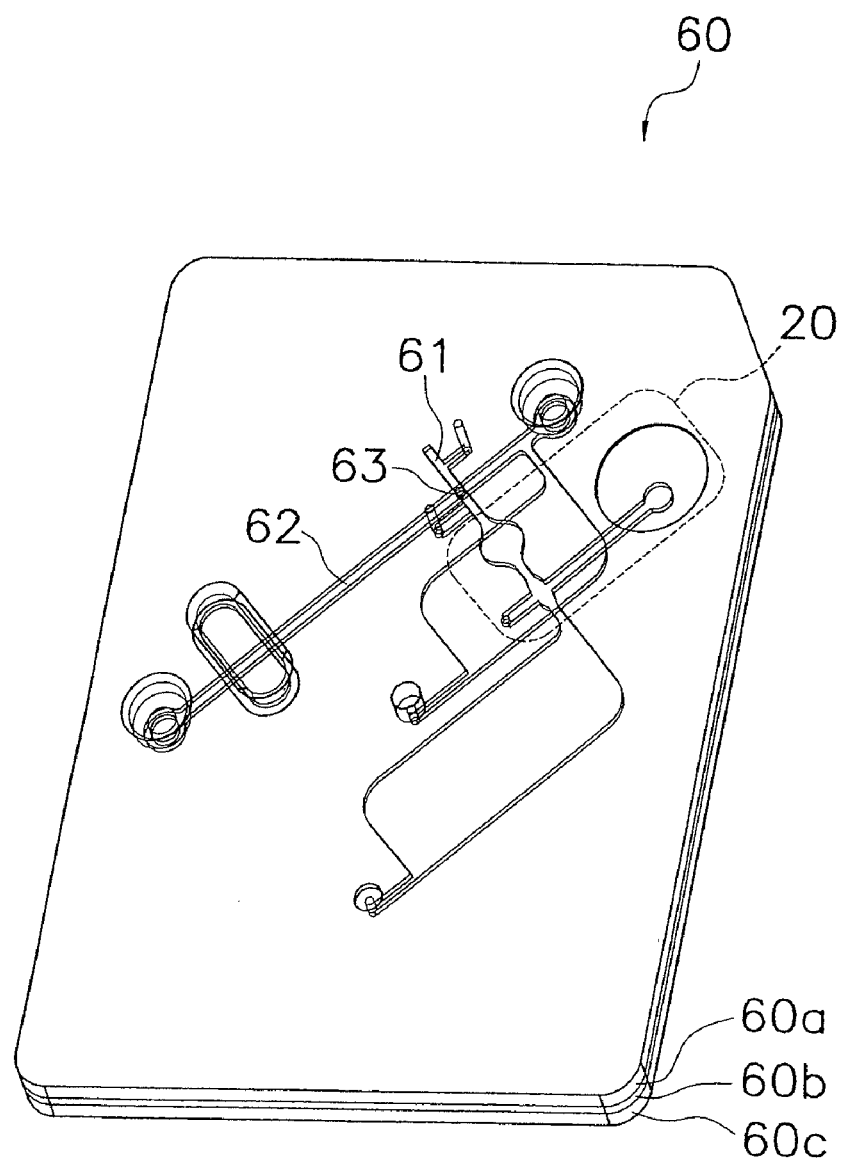
FIG. 5 is a perspective view of a structure of the electrophoresis chip according to another embodiment of the present invention.

The electrophoresis chip 60 according to the present embodiment is different from the electrophoresis chip 10 according to the first Embodiment in that a pretreatment unit 20 and other components are disposed on a substrate 60a as shown in FIG. 5. However, a basic structure of the chip 60 such as a sample introduction groove 61, an electrophoresis groove 62, and a through hole 63 is similar to that included in the sample introduction groove 11 and so on of the electrophoresis chip 10.

An electrophoresis chip 60 according to the present embodiment is a three-layered chip having a structure of laminating three substrates 60a to 60c that have the sample introduction groove 61, the electrophoresis groove 62 and the through hole 63, as shown in FIG. 5, and has the integrated pretreatment unit 20. The pretreatment unit 20 performs a pretreatment of destroying erythrocytes by mixing blood and a hemolysis diluent, for example.

Figure 6:
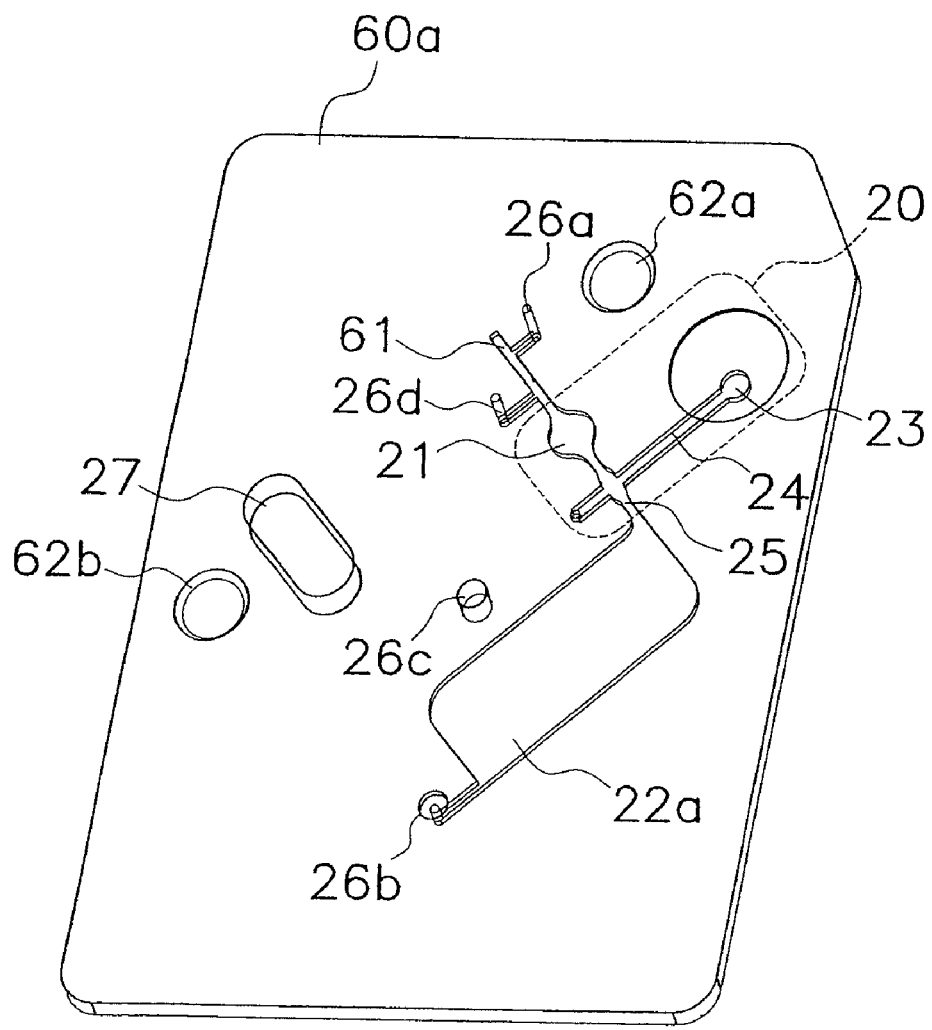
FIG. 6 is a perspective view of the individual substrate constituting the electrophoresis chip in FIG. 5.
Figure 7:
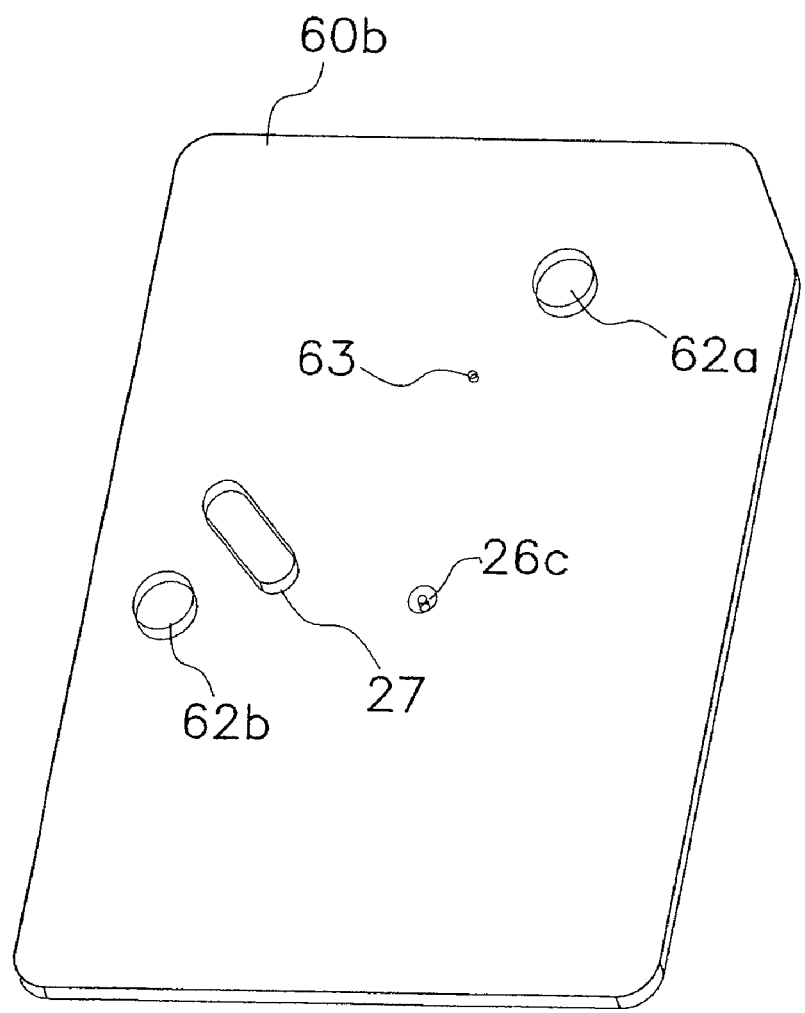
FIG. 7 is a perspective view of another of the individual substrates constituting the electrophoresis chip in FIG. 5.
Figure 8:
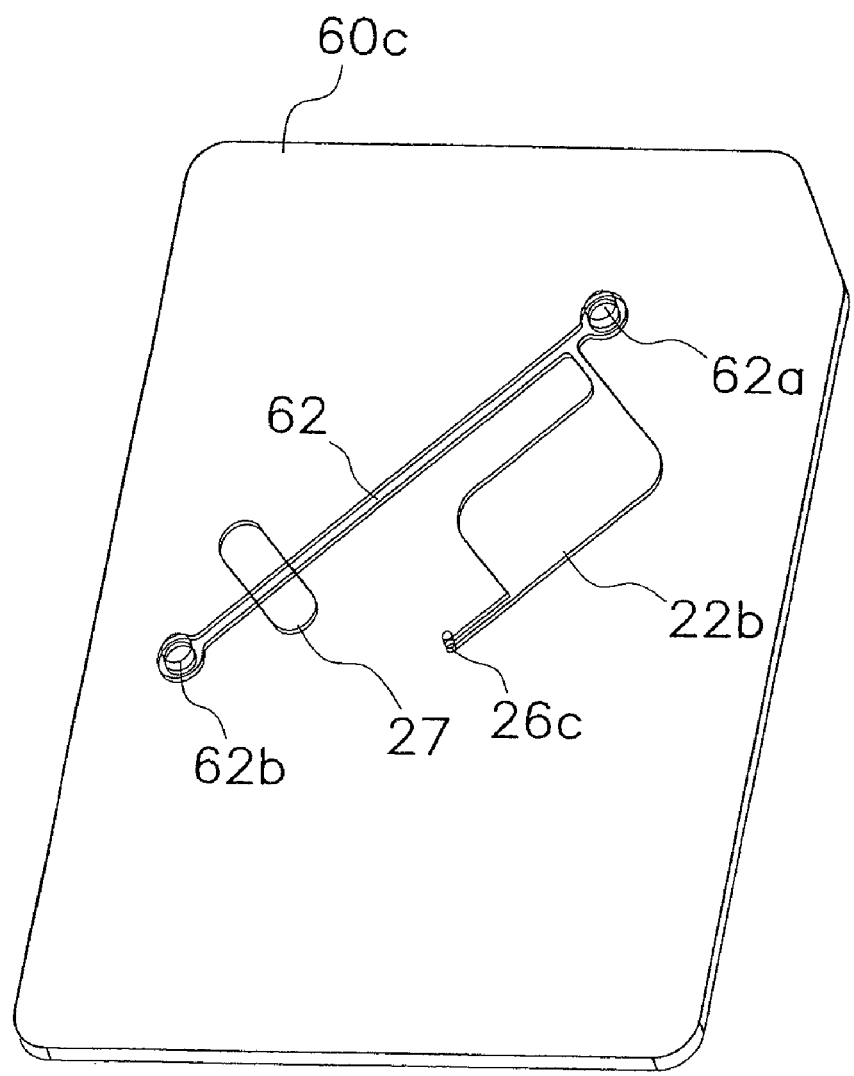
FIG. 8 is a perspective view of still another of the individual substrates constituting the electrophoresis chip in FIG. 5.

The substrate 60a is mainly formed, as shown in FIG. 6, of the sample introduction groove 61, the pretreatment unit 20, and a pretreatment liquid reservoir 22a. The pretreatment unit 20 includes a mix diffusion dilution unit 21 that mixes the pretreatment liquid and the sample "a" for diffusion and dilution, an introduction hole 23 to introduce sample "a" (for example, blood) before the pretreatment that is a base of sample "b" to be analyzed by electrophoresis, a sample-before-pretreatment introduction groove 24, and a pretreatment liquid introduction groove 25. The mix diffusion dilution unit 21 is disposed between the sample introduction groove 61 and the pretreatment liquid introduction groove 25, and mixes, diffuses and dilutes the sample "a" to be pretreated before the pretreatment with the pretreatment liquid. The introduction hole 23 is connected to the sample-before-pretreatment introduction groove 24 in the electrophoresis chip 60, and introduces the sample "a" that is dropped from the substrate 60a into the electrophoresis chip 60. In the sample-before-pretreatment introduction groove 24, the sample "a", which is introduced from the introduction hole 23, is filled up over the intersection with the pretreatment liquid introduction groove 25 up to the tip. The pretreatment liquid reservoir 22a is filled with the pretreatment liquid in advance, and the pretreatment liquid is flown into the pretreatment liquid introduction groove 25 at an appropriate or desirable time. The pretreatment liquid introduction groove 25 is placed at a position connecting the pretreatment liquid reservoir 22a and the mix diffusion dilution unit 21, and intersects with the above-described sample-before-pretreatment introduction groove 24.

Since the substrate 60a has the above-described structure, it is possible to perform a pretreatment of mixing the sample "a" with the pretreatment liquid to obtain the sample "b", and send the sample "b" from the mix diffusion dilution unit 21 to the sample introduction groove 61.

The substrate 60a is formed with air holes 26a to 26c that are opened when the sample, the pretreatment liquid, or the electrophoresis liquid is introduced at an appropriate or desirable time, openings 62a and 62b to which the electrodes are connected to apply a voltage between ends of the electrophoresis groove 62, and a detection unit 27 to detect components of the sample "b" separated in the electrophoresis chip 60 as well.

The substrate 60b is formed with the through hole 63 to communicate the sample introduction groove 61 and the electrophoresis groove 62 that are placed in different planes three-dimensionally, the air hole 26c penetrating through the openings 62a and 62b and the substrate 60c, and the detection unit 27. The through hole 63 is provided with the valve mechanism 14 in the same manner as the through hole 13 in the first Embodiment, and therefore, explanation is omitted.

The substrate 60c is formed with the electrophoresis groove 62, the openings 62a and 62b, an electrophoresis liquid reservoir 22b, the air hole 26c, and the detection unit 27. The openings 62a and 62b are formed at both ends of the electrophoresis groove 62, and to which electrodes are connected to apply a voltage to both the ends of the electrophoresis groove 62. The electrophoresis liquid reservoir 22b is filled with the electrophoresis liquid, and supplies the electrophoresis liquid to the electrophoresis groove 62 at an appropriate or desirable time when the air hole 26c is opened. The detection unit 27 detects separated components by electrophoresis in the electrophoresis groove 62 that is contained in the pretreated sample "b" dropped from the through hole 63. The following process is similar to that by the electrophoresis unit 50 according to the first Embodiment.

Analysis by the Electrophoresis Unit

In the electrophoresis unit including the electrophoresis chip 60 according to the present embodiment, processes are performed from the pretreatment of the sample to the analysis in the following procedure.

First, the sample "a" is introduced to fill the sample-before-pretreatment introduction groove 24 from the introduction hole 23. Next, the air holes 26b and 26d are opened to send a portion of the sample "a" that is disposed in the sample-before-pretreatment introduction groove 24 from the pretreatment liquid reservoir 22a with the pretreatment liquid to the mix diffusion dilution unit 21. The sample that is sent to the mix diffusion dilution unit 21 is mixed with the pretreatment liquid, and is diffused and diluted. Then, the sample "b" that is obtained by pretreating the sample "a" is introduced into the sample introduction groove 61 by opening the air hole 26a. Meanwhile, in the substrate 60c, the electrophoresis liquid is introduced into the electrophoresis groove 62 from the electrophoresis liquid reservoir 22b by opening the air hole 26c.

Figure 9:
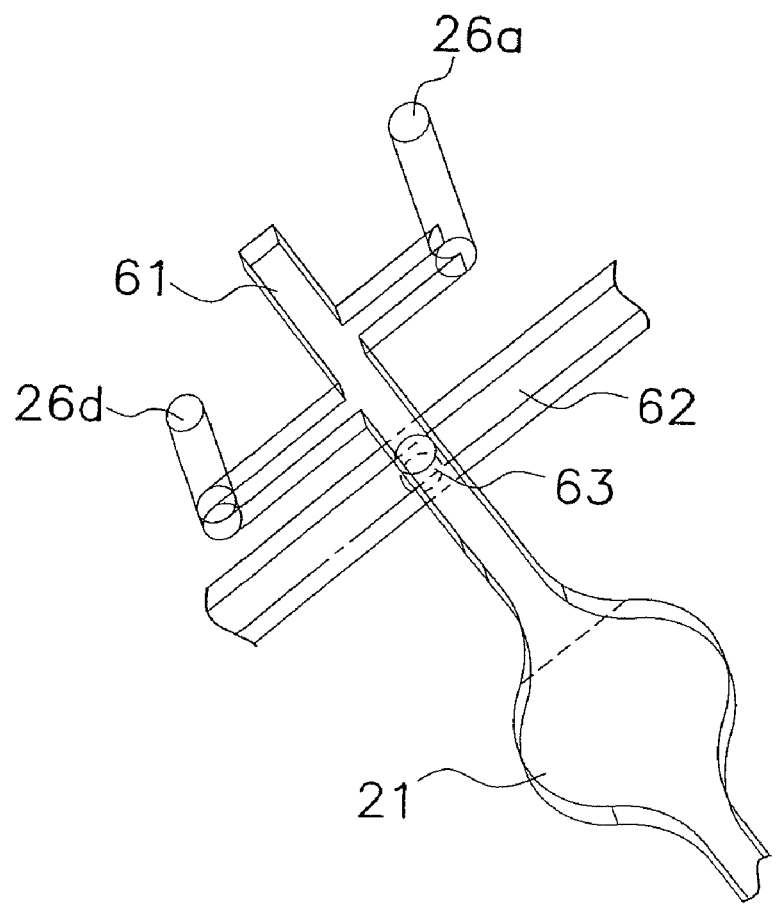
FIG. 9 is an enlarged view of the intersection between the sample introduction groove and the electrophoresis groove of the electrophoresis chip in FIG. 5.

When the sample "b" is introduced into the sample introduction groove 61, the laser light is applied to the light opening membrane formed at the through hole 63 shown in FIG. 9 to communicate the sample introduction groove 61 with the electrophoresis groove 62, so that the sample "b" to be analyzed by electrophoresis is moved to the electrophoresis groove 62.

In this state, the electrodes are connected to the openings 62a and 62b, and a voltage is applied between ends of the electrophoresis groove 62 to analyze the components of the sample "b" separated by electrophoresis. The analysis of the separated components of the sample "b" is performed by detecting them in the detection unit 27.

Features (1) In the electrophoresis chip 60 according to the present embodiment, the sample introduction groove 61 and the electrophoresis groove 62 are placed in the different planes three-dimensionally.

Typical conventional electrophoresis chips are configured such that the sample introduction groove and the electrophoresis groove are formed in one plane and intersect each other. In this structure, however, if a pretreatment unit that pretreats the sample in advance of analyzing components by electrophoresis is formed on the substrate on which the electrophoresis chip is formed, an area of the chip will be increased by the amount of the pretreatment unit formed thereon.

Therefore, in the electrophoresis chip 60 according to the present embodiment, the sample introduction groove 61 and the electrophoresis groove 62 are placed in different planes, i.e., on the different substrates 60a and 60b to form a three-dimensional structure.

Accordingly, since the pretreatment unit 20 is formed on the substrate 60a on which only the sample introduction groove 61 is formed, it is possible to restrain upsizing of the chip compared to the conventional structure in which the sample introduction groove 61 and the electrophoresis groove 62 are formed on one substrate. In other words, on the substrate 60a the electrophoresis groove 62 is not formed, but the sample introduction groove 61 only is formed. As a result, it is possible to form the pretreatment unit 20 without concern for a positional relationship with the electrophoresis groove 62, only considering a position where the sample introduction groove 61 is formed. Consequently, it is possible to obtain the integrated electrophoresis chip 60 while restraining upsizing of the chip, compared to the conventional structure in which the sample introduction groove 61 and the electrophoresis groove 62 are formed on one substrate.

(2) The electrophoresis chip 60 according to the present embodiment includes the pretreatment unit 20 that pretreats the sample in advance of electrophoresis.

Accordingly, it is possible to obtain a multifunctional chip by realizing a structure of the electrophoresis chip 60 in which the pretreatment unit 20 is formed on the substrate 60a.

Third Embodiment

A description is now provided for an electrophoresis chip according to the present invention with reference to FIGS. 10 to 13. It should be noted that components having functions to the same as those described in Embodiments 1 and 2 will be identified by the same reference numerals as the same ones for convenience of explanation, and the explanation will be omitted.

Figure 10:
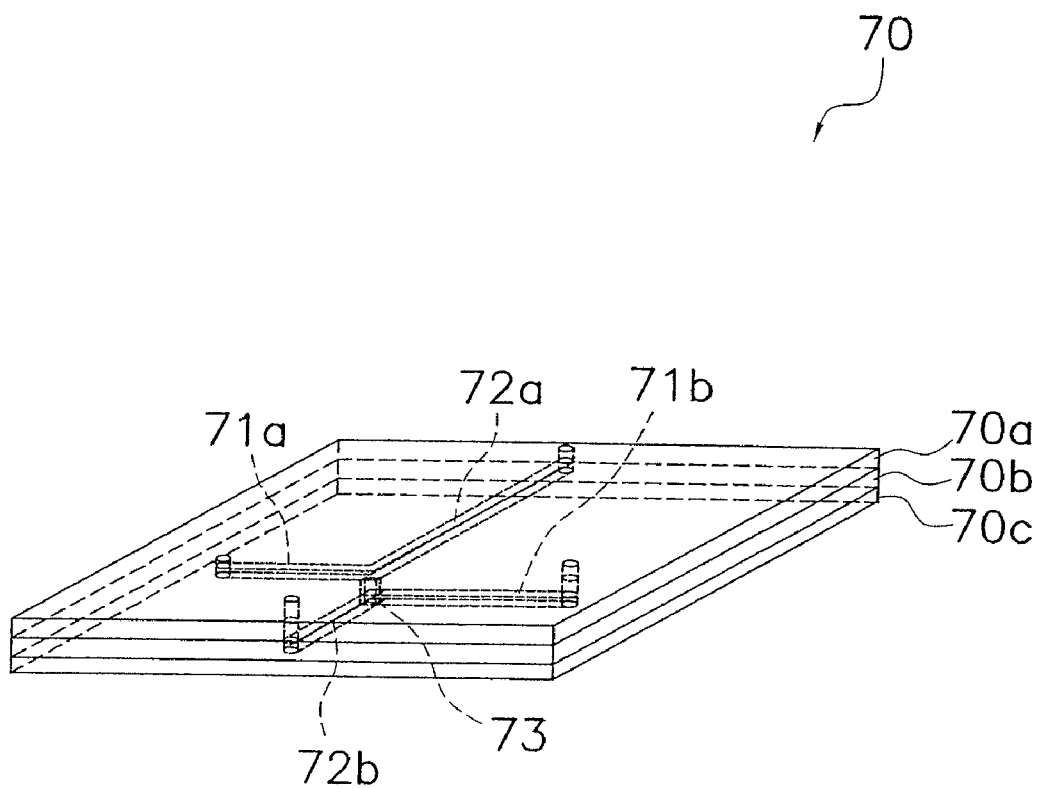
FIG. 10 is a perspective view of a structure of the electrophoresis chip according to a still further embodiment of the present invention.
Figure 11:
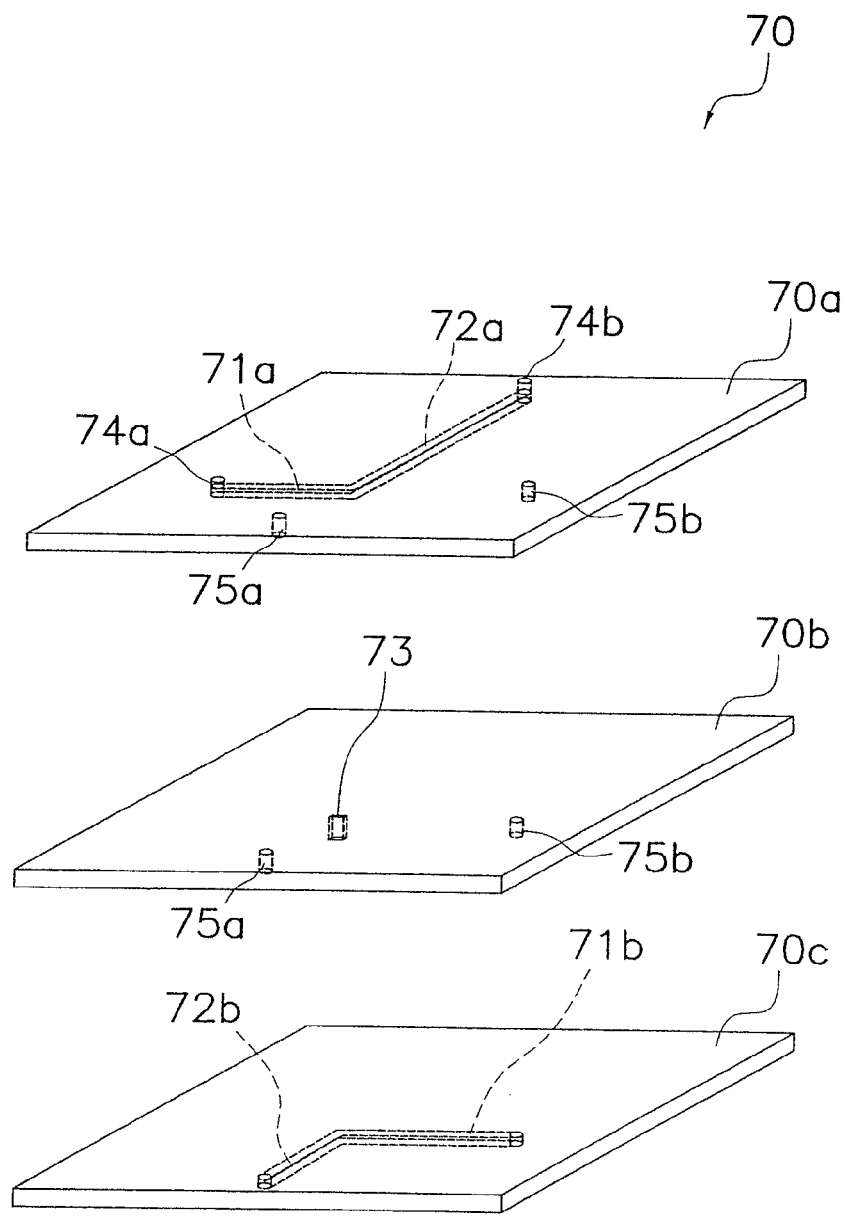
FIG. 11 is an exploded perspective view of the various substrates that constitute the electrophoresis chip in FIG. 10.

An electrophoresis chip 70 according to present embodiment has a commonality with the electrophoresis chip 10 in Embodiment 1 in that the sample introduction groove and the electrophoresis groove are formed on the three substrates 70a to 70c as shown in FIG. 10 and FIG. 11. However, in the electrophoresis chip 70 according to the present embodiment, it differs from the electrophoresis chip 10 in that the sample introduction groove and the electrophoresis groove are halved respectively, i.e., the first sample introduction groove 71a and the first electrophoresis groove 72a are formed on the substrate 70a, and the second sample introduction groove 71b and the second electrophoresis groove 72b are formed on the substrate 70c.

In the electrophoresis chip 70 according to present the embodiment, as described above, the first sample introduction groove 71a and the second sample introduction groove 71b are formed in different planes (on the substrate 70a and the substrate 70c) and are connected for communication with each other via a through hole 73 at their ends.

Similarly, the first electrophoresis groove 72a and the second electrophoresis groove 72b are formed in different planes (on the substrate 70c and the substrate 70a), and are connected with each other for communication via the through hole 73 at their ends, too.

In summary, the first sample introduction groove 71a, the second sample introduction groove 71b, the first electrophoresis groove 72a, and the second electrophoresis groove 72b are connected with each other via the common through hole 73 for mutual communication.

Figure 12:
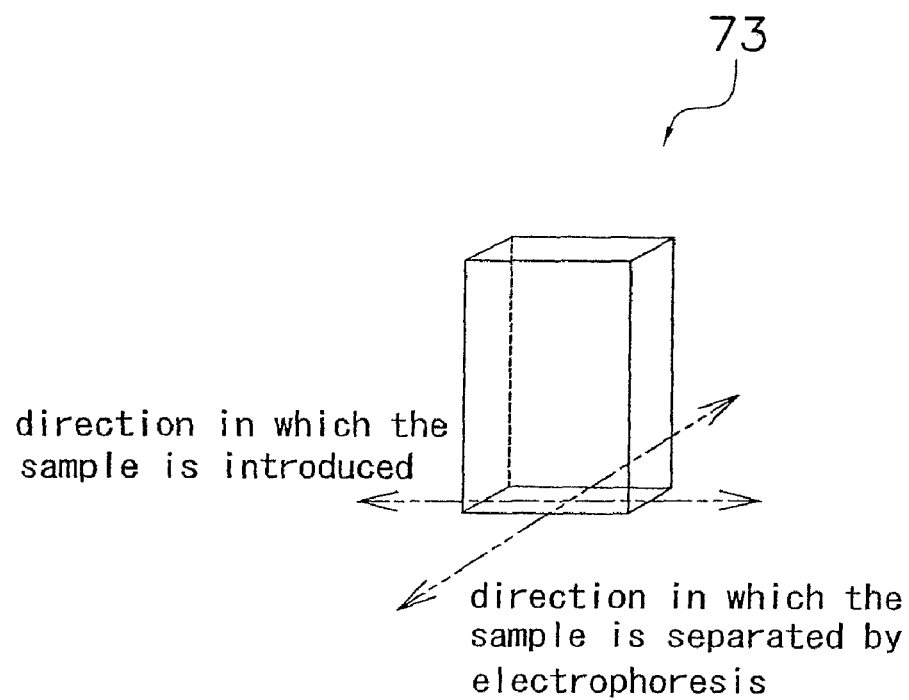
FIG. 12 is an enlarged view of a through hole formed in the electrophoresis chip in FIG. 10.

The through hole 73 is formed on the substrate 70b, on which neither the groove 71a, 71b, 72a, nor 72b is formed. The through hole 73 has a cross section with different lengths according to directions such as a direction in which the samples are introduced along the first and second sample introduction grooves 71a and 71b that are formed on an almost straight line and a direction in which the sample is separated by electrophoresis along the first and second electrophoresis grooves 72a and 72b that are formed on an almost straight line, as shown in FIG. 12. More specifically, the through hole 73 has a cross section of rectangle, wherein narrow sides of the rectangle is placed along a direction in which the sample is separated by electrophoresis, and wide sides of the rectangle are placed along a direction in which the sample is introduced.

Features (1) In the electrophoresis chip 70 according to present embodiment, as shown in FIG. 10 and FIG. 11, the first sample introduction groove 71a and the second sample introduction groove 71b are placed in different planes (on the substrates 70a and 70c). Meanwhile, the first electrophoresis groove 72a and the second electrophoresis groove 72b are placed in different planes (on the substrates 70c and 70a), too. The grooves 71a, 71b, 72a, and 72b are connected with each other via the through hole 73 for mutual communication.

Accordingly, since the sample introduced into the first and second sample introduction grooves 71a and 71b is also introduced into the through hole 73, it is possible to separate a certain amount of sample introduced into the through hole 73 for analysis by applying a voltage between ends of the first and second electrophoresis grooves 72a and 72b after introducing the sample.

Consequently, it is possible to perform the separation and analysis by electrophoresis by reliably ensuring the sample introduced into the common through hole 73. As a result, it is possible to reduce the amount of diffusion into electrophoresis liquid (diffusion ratio) of the sample introduced into the through hole 73 and to perform the separation and analysis by ensuring a stable amount of sample for every analysis compared to the conventional electrophoresis chip in which the sample introduction groove and the electrophoresis groove simply intersect with each other in one plane.

(2) In the electrophoresis chip 70 according to the present embodiment, the through hole 73 that communicates the grooves 71a, 71b, 72a, and 72b with each other has a cross section where a length in a direction in which the sample is separated by electrophoresis is shorter than a length in a direction in which the sample is introduced.

Since the through hole 73 is configured to have the cross section with different lengths in the direction in which the sample is separated and in the direction in which the sample is introduced, it is possible to smoothly move the sample introduced into the through hole 73 in an electrophoretic direction when the sample is separated by electrophoresis, not diffusing the sample in other directions. As a result, a width of the peak to be detected becomes narrow, and a highly precise analysis output can be obtained.

(3) In the electrophoresis chip 70 according to present embodiment, the first sample introduction groove 71a and the first electrophoresis groove 72a are formed on the substrate 70a, and the second sample introduction groove 71b and the second electrophoresis groove 72b are formed on the substrate 70c.

Accordingly, the electrophoresis chip 70 according to present embodiment can be realized having a structure in which the substrate 70b for forming the through hole 73 is sandwiched as one within the three substrates 70a to 70c. As a result, it is possible to cut down on costs by simplifying the structure.

Experiment 1

Here, a description will be made on the outcome of the separation and analysis of samples by electrophoresis with the electrophoresis chip 70 according to present embodiment with reference to FIG. 13(a) through FIG. 13(d).

As a sample, a mixture was used that included substances having the following final concentrations: 25.0 mM for mesityl oxide; 12.5 mM for tryptophan, 25.0 mM for vitamin B1 hydrochloride, and 0.1 mM for uric acid-sodium with.

Figure 13A:
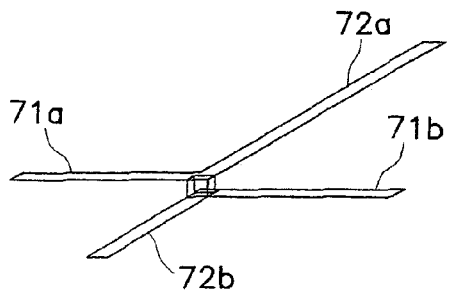
FIG. 13 is an explanatory view of a process flow using the electrophoresis chip in FIG. 10.
Figure 13B:
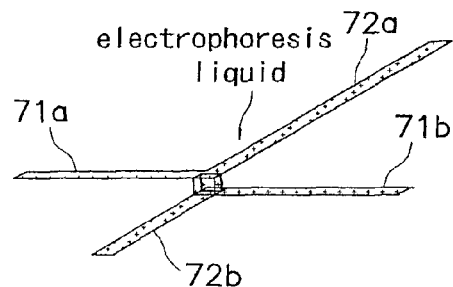
Figure 13C:
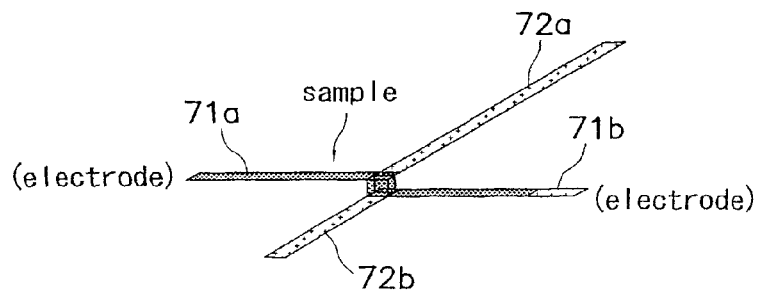
Figure 13D:
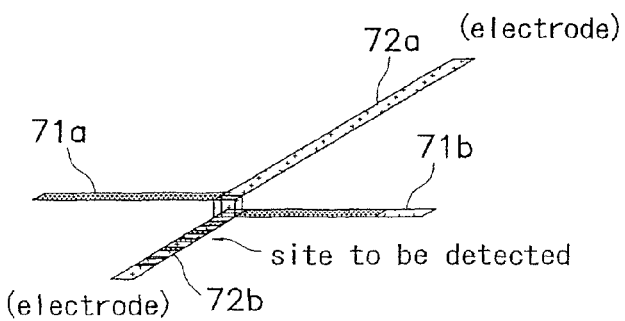

First, as shown in FIG. 13(a), a water-soluble electrophoresis liquid such as phosphate buffer (pH 8.7) was injected by pressure into the grooves 71a, 71b, 72a, and 72b of the electrophoresis chip 70. Consequently, as shown in FIG. 13(b), the grooves 71a, 71b, 72a, and 72b were filled with the electrophoresis liquid.

The sample is introduced into the opening 74a formed at the end of the first sample introduction groove 71a. Next, electrodes are connected to the opening 74a (refer to FIG. 11) formed at the ends of the first sample introduction groove 71a and the opening 75b (refer to FIG. 11) formed at the ends of the second sample introduction groove 71b. Then a voltage of 1.5 kV is applied to the electrodes, so that appropriate portions of the sample are moved via electrophoresis through the first sample introduction groove 71a to the through hole 73 and into the second sample introduction groove 71b.

After the introduction of the sample, the voltage was stopped from being applied to the first and second sample introduction grooves 71a and 71b, and a voltage was applied between ends (openings 74b and 75a) of the first and second electrophoresis grooves 72a and 72b to start the separation and analysis by electrophoresis. The voltage was applied at 1.5 kV for 15 minutes.

At the same time as the application of voltage, the detection was performed at 280 nm at predetermined detection positions in the second electrophoresis groove 72b formed on the substrate 70c.

As a result, 4 peaks were detected in the order of vitamin B1 hydrochloride, mesityl oxide, tryptophan, and uric acid-sodium.

Different absorption spectrums of different substances that had confirmed were used to judge the substances.

Other Embodiments

Although one embodiment of the present invention is described above, the present invention is not limited to the embodiment, and various changes may be made without departing from the scope of the invention.

(A) In the first and second embodiments, an example was described in which the sample introduction groove 11, the electrophoresis groove 12, and the through hole 13 were formed on different substrates and then the substrates were combined to form a structure of the electrophoresis chip 10. However, the present invention is not limited to this example.

For example, the sample introduction groove 11 and the through hole 13 may be formed on one substrate, and the electrophoresis groove 12 and the through hole 13 may be formed on one substrate. Alternatively, all of the structures may be formed on one substrate.

(B) In the first embodiment, an example was described in which the sample introduction groove 11 and the electrophoresis groove 12 were placed in different planes three-dimensionally, and the through hole 13 that communicated the sample introduction groove 11 with the electrophoresis groove 12 was provided with the valve mechanism 14. However, the present invention is not limited to this example.

For example, the sample introduction groove 11 and the electrophoresis groove 12 may be formed in one plane, and the sample introduction groove 11 and the electrophoresis groove 12 may be provided with the valve mechanism 14 at their intersection.

In this example, too, it is possible to prevent the electrophoresis liquid and the sample from being mixed at a stage in advance of the start of electrophoresis by changing the valve mechanism 14 to an open state immediately before applying a voltage between ends of the electrophoresis groove 12.

(C) In the first and second embodiments, an example was used in which the aqueous solution was used as an electrophoresis liquid. However, the present invention is not limited to this example.

For example, a gelatinous electrophoresis liquid may be used.

However, it is preferable to use the aqueous solution as an electrophoresis liquid in a sense that the present invention can be used more effectively because the valve mechanism of the through hole 13 is especially effective in preventing the diffusion of sample even if the electrophoresis liquid is the aqueous solution that is likely to be mixed with the sample and to be diffused.

(D) In the first and second embodiments, an example was described in which the sample introduction groove 11, the electrophoresis groove 12 and so on were formed by etching. However, the present invention is not limited to this example.

For example, the sample introduction groove 11 and/or the electrophoresis groove 12 may be formed by other methods such as machining. However, it is preferable to form the sample introduction groove 11, the electrophoresis groove 12 and so on by etching to ensure the processing accuracy while considering the recent size reduction of chips.

(E) In the first and second embodiments, an example was described in which the valve mechanism 14 included the light opening membrane 14a and the irradiation unit 14b, and the valve mechanism 14 was opened by destroying the light opening membrane 14a by the laser light applied from the irradiation unit 14b. However, the present invention is not limited to this example.

For example, the valve such as a membrane may be destroyed by a mechanical means or an electrical means for opening, without using the optical means in above described embodiments.

The valve mechanism 14 may employ a structure in which it can not close itself once it is opened as in Embodiments, or a structure in which it can be opened and closed repeatedly. However, the valve mechanism that can be repeatedly opened and closed is preferable because it can be employed in a relatively expensive electrophoresis chip to restrain increase in cost.

(F) In the first and second embodiments, an example was described in which a cross section of the through hole 13 that communicates the sample introduction groove 11 with the electrophoresis groove 12 had a circular shape. However, the present invention is not limited to this example.

For example, a through hole that has a cross-sectional shape of quadrangle may be used.

(G) In the third embodiment, an example was described in which a cross section of the through hole 73 was rectangle that communicated the first sample introduction groove 71a with the second sample introduction groove 71b, and the first electrophoresis groove 72a with the second electrophoresis groove 72b. However, the present invention is not limited to this example.

For example, a through hole having a cross-sectional shape of circle may be used, as in the case of the through hole 13 described in the first and second embodiments.

However, if the cross section is a rectangle having short sides in a direction in which the sample is separated by electrophoresis as in Embodiment 3, it is possible to reduce the diffusion of sample during electrophoresis as described above, thereby to perform a more highly precise detection.

(H) In third embodiment, an example was described in which the sample introduction groove 71a and the electrophoresis groove 72a were formed in one plane (on the substrate 70a). However, the present invention is not limited to this example.

For example, the sample introduction groove 71a and the electrophoresis groove 72a may be formed in different planes.

(I) In third embodiment, an example was described in which the first sample introduction groove 71a and the second sample introduction groove 71b were located on an approximately straight line, and the first electrophoresis groove 72a and the second electrophoresis groove 72b were located on an approximately straight line. However, the present invention is not limited to this example.

For example, the electrophoresis chip 10 shown in FIG. 3 may be used such that a voltage is applied to the opening 11a and the opening 12b and the sample is introduced into a half of the sample introduction groove 11 and a half of the electrophoresis groove 12 in the sample introduction process, and a voltage is applied to the opening 11b and the opening 12a for separation by electrophoresis in the separation process. In other words, one part of the sample introduction groove 11 shown in FIG. 3 and one part of the electrophoresis groove 12 may be utilized as sample introduction grooves, and the other part of the sample introduction groove 11 and the other part of the electrophoresis groove 12 may be used as electrophoresis grooves.

As described above, even if the sample introduction groove and electrophoresis groove are figured to be bent in the middle, it is possible to restrain the diffusion of the sample introduced into the through hole 13 and perform a separation process with a stable amount of the sample introduced into the through hole 13 every time.

(J) In the third embodiment, an example was described in which the first and second sample introduction grooves 71a and 71b, the first and second electrophoresis grooves 72a and 72b and the through hole 73 were formed on the substrates 70a to 70c. However, the present invention is not limited to this example.

For example, the pretreatment unit 20 shown in FIG. 6 may be formed on the substrate 70a. In this example, a sample to be analyzed can be pretreated on the electrophoresis chip simultaneously.

(K) In the first, second and third embodiments, an example was described in which an electrophoresis chip of what is called cross type was used in which the sample introduction groove and the electrophoresis groove were crossed with each other. However, the present invention is not limited to this example.

For example, the present invention can be applied to an electrophoresis chip of what is called double T type in which two sample introduction grooves are connected to one electrophoresis groove at different portions.

INDUSTRIAL APPLICABILITY

The present invention relates to an electrophoresis chip and an electrophoresis unit having the same to analyze blood components, protein, or nuclei acids.

What is claimed is:
1. An electrophoresis chip, comprising:
a sample introduction groove into which a sample is introduced;
an electrophoresis groove located along a direction that intersects with the sample introduction groove, having both ends to which a voltage is applied to separate the sample by electrophoresis; and
a valve mechanism located at the intersection between the electrophoresis groove and the sample introduction groove,
wherein the valve mechanism can be changed into an open state by using optical means, and wherein the valve mechanism includes a membrane containing dye and being capable of being destroyed by causing the dye to absorb heat generated due to light irradiation; and wherein the valve mechanism can be opened and closed repeatedly.

2. The electrophoresis chip as set forth in claim 1, wherein an electrophoresis liquid is introduced into the electrophoresis groove, and the electrophoresis liquid is an aqueous solution.

3. The electrophoresis chip as set forth in claim 1, further comprising:
- a first substrate on which the electrophoresis groove is formed; and
- a second substrate on which the sample introduction groove is formed.

4. The electrophoresis chip as set forth in claim 1, wherein the electrophoresis groove and sample introduction groove lie within the same plane within the electrophoresis chip.

* * * * *